US00PP09757P

United States Patent [19]

Lopez

[11] Patent Number: Plant 9,757

[45] Date of Patent: Dec. 24, 1996

[54] STRAWBERRY PLANT NAMED 'AIRES'

[75] Inventor: Jose M. A. Lopez, Navarra, Spain

[73] Assignee: Plantas de Navarra, S.A., Navarra, Spain

[21] Appl. No.: 512,886

[22] Filed: Aug. 9, 1995

[51] Int. Cl.[6] ..... A01H 5/00

[52] U.S. Cl. ..... Plt./49

[58] Field of Search ..... Plt./48, 49

[56] References Cited

U.S. PATENT DOCUMENTS

P.P. 5,266 7/1984 Bringhurst et al. ..... Plt./49

*Primary Examiner*—James R. Feyrer

*Attorney, Agent, or Firm*—Christie, Parker & Hale, LLP

[57] ABSTRACT

A strawberry plant producing conical-shaped fruit and having inflorescence extending beneath the foliage.

6 Drawing Sheets

BACKGROUND OF THE INVENTION

The new variety of strawberry was created in a breeding program by my crossing two parents from among a group of seedlings which were obtained from a free pollination of 32 different varieties and seedlings; in particular, by crossing as seed parent a variety designated 86-037 and as a pollen parent a variety designated 86-096. Both parental varieties are proprietary and have not been commercialized.

The resulting seedling of the new variety was grown and asexually reproduced by runners in Soria, Spain, 3°W., 41°N., 3000 feet elevation. Clones of the new variety were further asexually propagated and extensively tested. This propagation and testing has demonstrated that the combination of traits disclosed herein which characterize the new variety are fixed and retained true to type through successive generations of asexual reproduction.

SUMMARY OF THE INVENTION

The present invention relates to a new and distinct strawberry variety genus *L. fragaria.* The varietal denomination of the new variety is 'Aires'. Among the charcteristics which distinguish the new variety from other varieties of which I am aware are a combination of traits which include inflorescence that appears beneath the foliage and abundant production of conical-shaped fruit.

COMPARISON TO CLOSEST VARIETY

The new variety is closest to the variety 'Selva' (U.S. Plant Pat. No. 5,266), but is distinguished therefrom by the following characteristics possessed by 'Aires' which are different than, or not possessed by, Selva.

1. 'Selva' plant is flatter and less vigorous than 'Aires'.

2. Terminal leaflet of 'Selva' is longer than broad whereas in 'Aires' it is as long as broad.

3. Shape of the terminal leaflet base of 'Selva' is acute and in 'Aires' it is rounded.

4. Inflorescence in 'Selva' is level with foliage and in 'Aires' it is beneath.

5. 'Selva's petals are as long as broad. In 'Aires' the petals are broader than long. The petal size of 'Aires' is about 10 to 11 mm wide and about 8 to 9 mm long, whereas 'Selva' petals are about 9 mm wide and about 9 mm long.

6. 'Selva' Fruit is bigger than 'Aires' fruit.

7. Fruit of 'Selva' is less bright but more even in color than 'Aires'. As can be seen by the comparison in FIGS. 8 and 9, the color of 'Selva' is darker than that of the new variety (designated 9079060).

As can be seen by commparison of FIGS. 9 and 10, the fruit color of new variety is brighter red than that of 'Selva'. The difference in the core is also evident from the illustrations.

8. Insertion of achenes in fruit is level with surface whereas in 'Aires' insertion is below surface.

9. Insertion of calyx in fruit is level in 'Selva' whereas in 'Aires' it is in a basin.

10. 'Selva' fruit is firmer than 'Aires'.

11. Flesh color of 'Selva' is orange-red and is pale red in 'Aires'.

12. 'Selva' fruit is less acid than 'Aires'.

BRIEF DESCRIPTION OF ILLUSTRATION

The accompanying photographs show typical specimens of the new variety, designated 90-79-060 in the illustrations, including fruit, foliage and flower, in color as nearly true as it is reasonably possible to make in color illustrations of this character.

Figure 1:
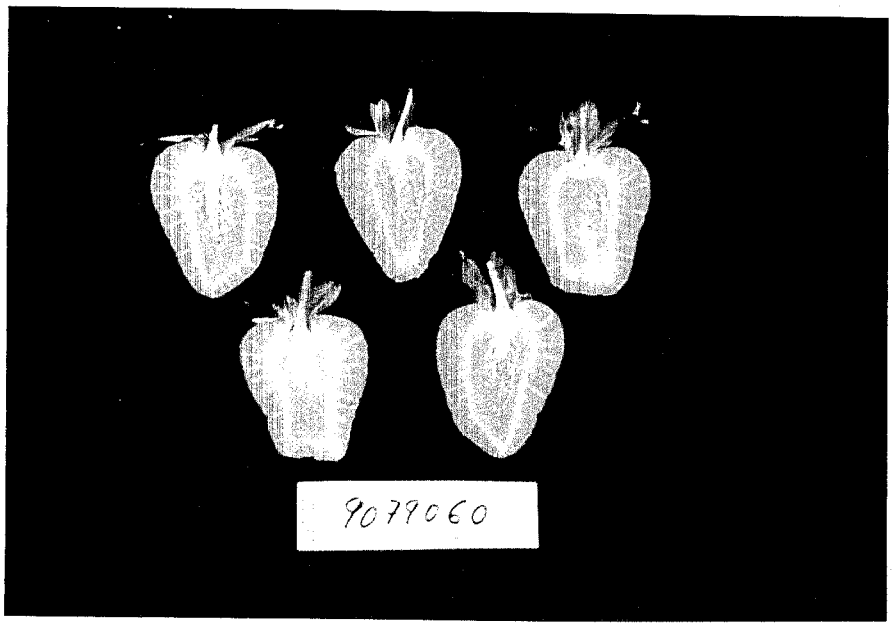
FIG. 1 shows typical fruit in cross section illustrating the typical flesh and flesh coloration, conspicuous core and core cavity and conical shape.
Figure 2:
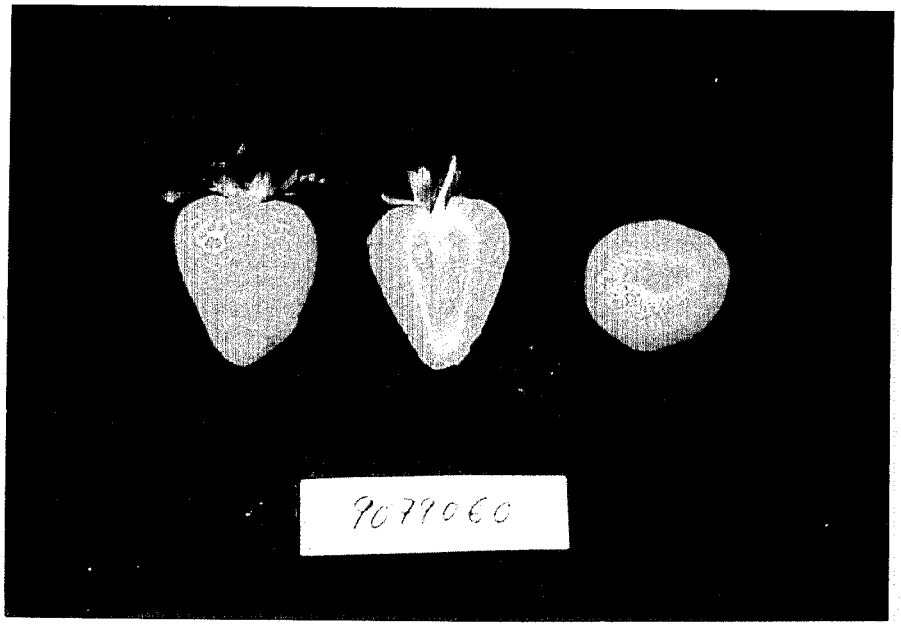
FIG. 2 shows whole and sliced, detached fruit.
Figure 3:
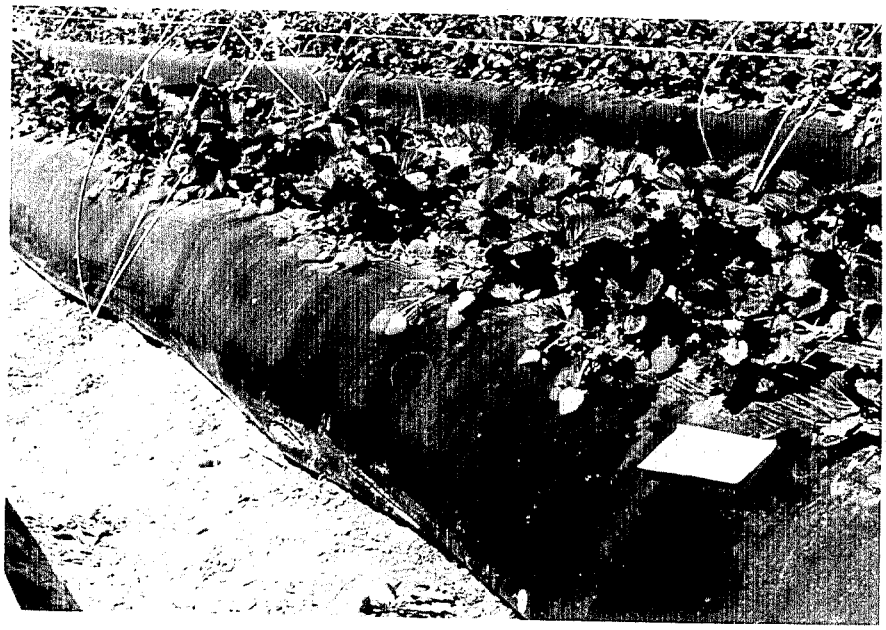
FIGS. 3 and 4 show the fruit against the background of the top surface of the foliage.
Figure 4:
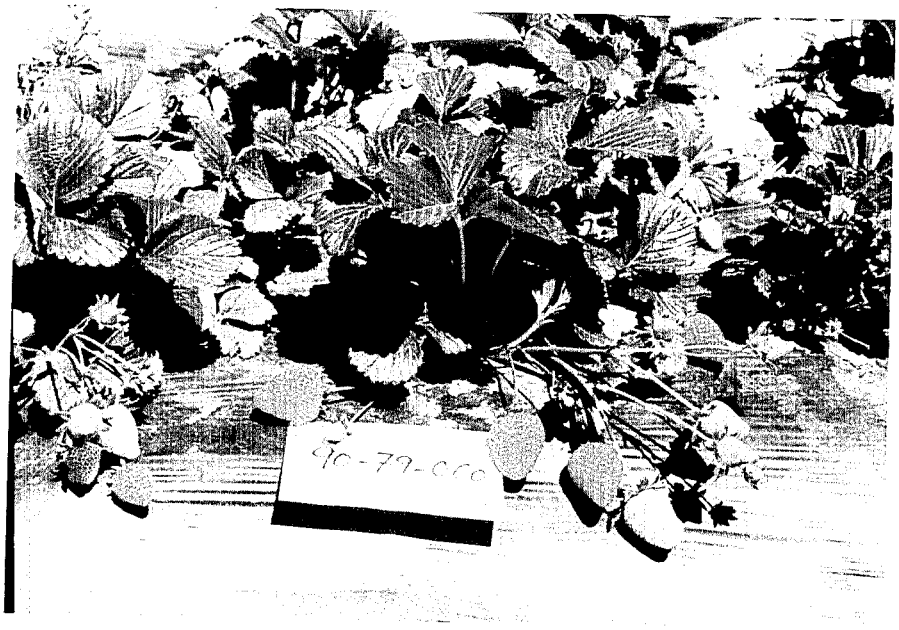
Figure 5:
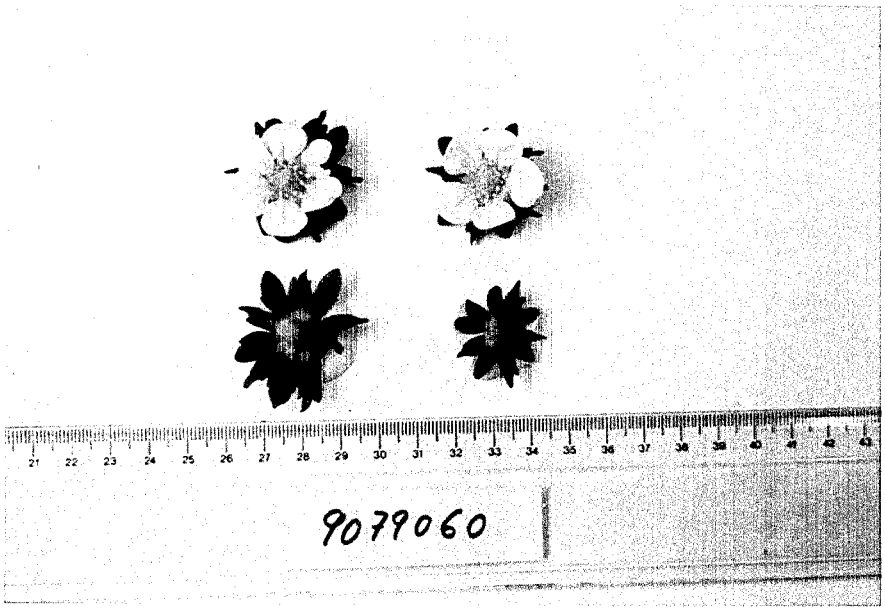
FIG. 5 shows the flower and reproductive organs of the new variety.
Figure 6:
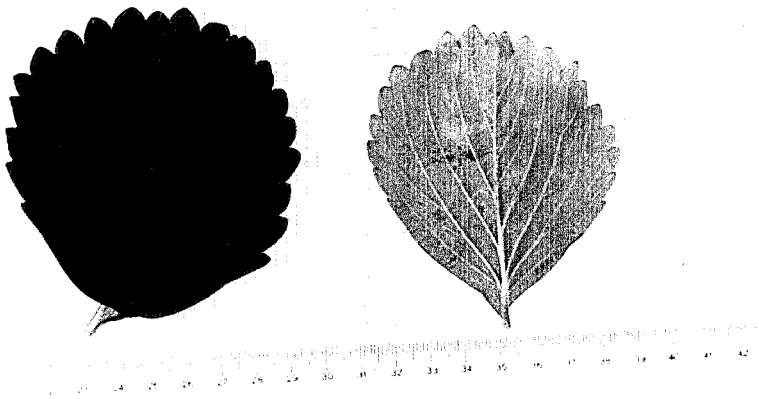
FIG. 6 shows the top and undersurface of a typical foliose of the new variety.
Figure 7:
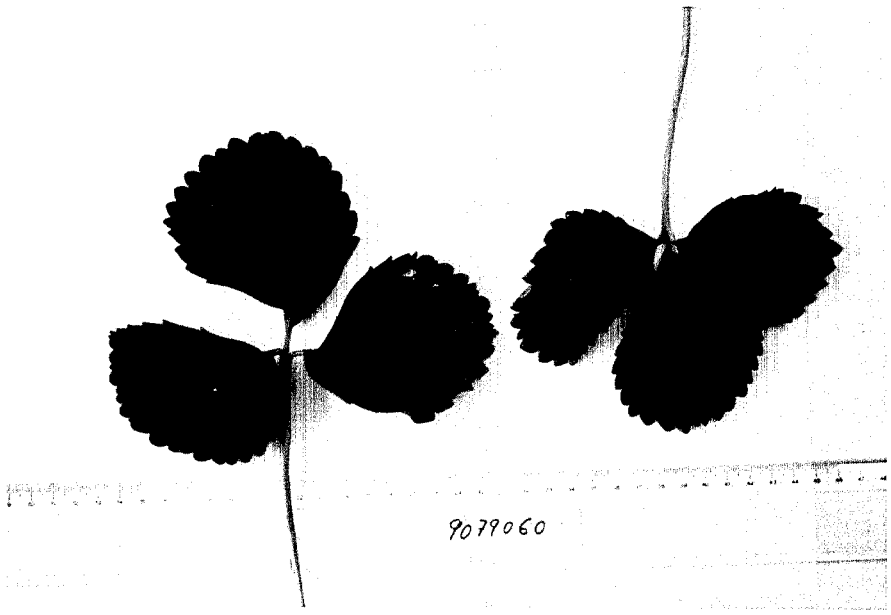
Figure 8:
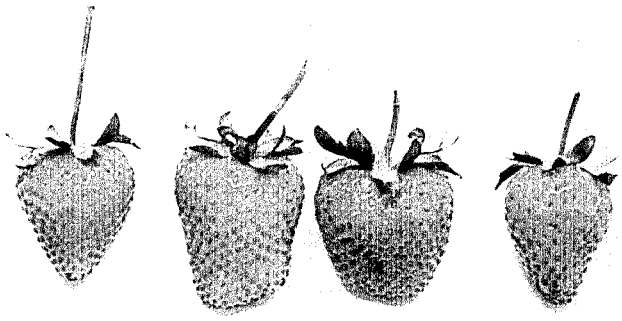
Figure 9:
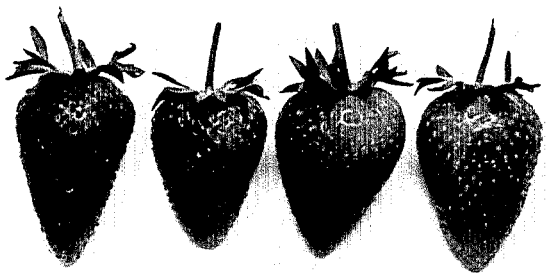
Figure 10:
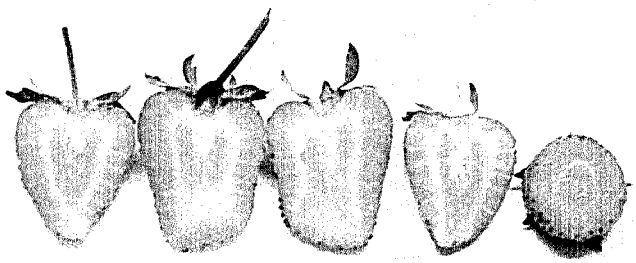
Figure 11:
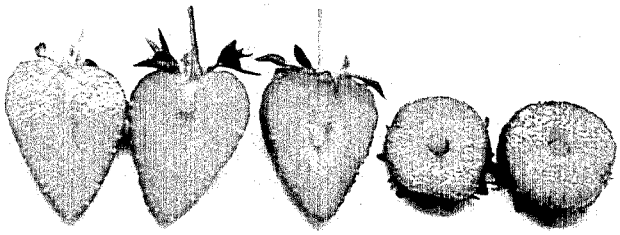

FIG. 7 illustration shows a typical leave of the new variety;

FIGS. 8 and 9 show the fruit of the new variety (designated 9079060) and 'Selva', respectively; and FIGS. 10 and 11 show cross-section of the fruit of the new variety (designated 9079060) and 'Selva', respectively.

DESCRIPTION OF THE NEW VARIETY

The following detailed description of the new variety is based upon observations taken of plants and fruit grown "underglass", i.e. undertunnel, in a farm in Cartaya (Huelva), Spain, 7°W., 37°N., 45 feet elevation.

The description is in accordance with UPOV terminology and the color terminology herein is in accordance with The Royal Horticultural Society Colour Chart (R.H.S.C.C.). The color descriptions and other phenotypical descriptions may deviate from the stated values and descriptions depending upon variation in environmental, seasonal, climatic and cultural conditions.

Propagation

The new variety is principally propagated by way of runners. Although propagation by runners is presently preferred, other known methods of propagating may be used. Strawberry plants root well after transplanting.

The term "blistering" used herein refers to the texture or rugosity inherent to leaves and is generally a constant characteristic.

'Aires' is a day neutral variety. It is about as strongly day-neutral as Selva, and less strong than 'Irvine' (U.S. Plant Pat. No. 7,172) or Fern (U.S. Plant Pat. No. 5,267). 'Aires' does not need any additional treatment to assure a sufficient flowering.

Production: Plant issued from high elevation nursery.
*Date of planting.*—Jun. 30, 1993.
*Number of repetitions.*—1.
*Plants per repetition.*—40.

| CULTIVAR | G/P1 1[a] | G/P1 2[a] | TOTAL YIELD G/P1 | TOTAL YIELD KG/HA | SIZE G/P1 |
|---|---|---|---|---|---|
| AUTUMN 1993: 09-14/11-22. 9 HARVESTINGS | | | | | |
| AIRES | 194 | 45 | 239 | 8.640 | 18 |
| SELVA | 75 | 28 | 103 | 3.708 | 18.5 |
| SPRING 1994: 05-02/07-18 10 HARVESTINGS | | | | | |
| AIRES | 823 | 147 | 970 | 34.920 | 18 |
| SELVA | 729 | 119 | 848 | 30.528 | 18 |

The following is a comparison of features of the new variety 'Aires', and of 'Selva'.

| | 'AIRES' | 'SELVA' |
|---|---|---|
| Firmness (kg) | 1.1 | 1.2 |
| PH | 3.09 | 3.12 |
| Acidity as Anhidride Citric (%) | 1.00 | 0.93 |
| Soluble Solids (° Brix) | 5.2 | 7.7 |

As can be seen, the fruit of 'Selva' is firmer and less acid than that of 'Aires'.

The following additional information is provided to further describe the new variety.

Plant:
*Habit.*—Flat globose.
*Density.*—Medium.
*Vigour.*—Medium.
*Height.*—About 16 cm.
*Width.*—About 21 cm.

Leaf:
*Green color of upper side.*—Dark.
*Length.*—About 9.5 cm.
*Width.*—About 12.5 cm.
*Cross Section.*—Slightly convex.
*Blistering.*—Medium.
*Number of leaflets.*—Three.

Terminal leaflet:
*Length/width ratio.*—As long as broad.
*Length.*—About 6 cm.
*Width.*—About 6 cm.
*Shape of base.*—Rounded.
*Shape of teeth.*—Obtuse.

Petiole:
*Position of hairs.*—Outwards.
*Length.*—About 9.2 cm.

Stipule:
*Anthocyanin coloration.*—Weak.

Stolons:
*Number.*—Few.

Anthocyanin coloration: Medium.
*Thickness.*—Thick.
*Pubescence.*—Medium.

Inflorescence:
*Position relative to foliage.*—Beneath.

Flower:
*Size.*—Medium.
*Size of calyx relative to corolla.*—Smaller.
*Size of inner calyx relative to outer.*—Same size.
*Spacing of petals.*—Overlapping.

Petal:
*Length/width ratio.*—Broader than long.

Fruiting truss:
*Attitude.*—Semi-erect.

Fruit:
*Ratio of length/maximum width.*—Longer than broad.
*Primary fruit.*—
*Length.*—About 4.6 cm.
*Width.*—About 3.5 cm.
*Secondary fruit.*—
*Length.*—About 4 cm.
*Width.*—About 2.7 cm.
*Size.*—Medium.
*Predominant shape.*—Conical.
*Difference in shapes between primary and secondary fruits.*—Moderate.
*Band without achenes.*—Absent or very narrow.
*Color of achenes.*—Amber red.
*Unevenness of surface.*—Absent of very weak.
*Color.*—Red.
*Evenness of color.*—Slightly uneven.
*Glossiness.*—Strong.
*Insertion of achenes.*—Below surface.
*Insertion of calyx.*—In a basin.
*Pose of the calyx segment.*—Reflexed.
*Size of calyx in relation to fruit diameter.*—Larger.
*Adherence of calyx.*—Strong.
Firmness.—Firm.
*Color of flesh.*—Pale rose.
*Evenness of color of the flesh.*—Slightly uneven.
*Sweetness.*—Medium.
*Acidity.*—Strong.
*Time of flowering.*—Very early.
*Time of ripening.*—Very early.
*Type of bearing.*—Fully remontant.
*Chilling.*—Chilling to induce flower production is desirable for the new variety. Note: The growing period in Huelva, Spain though obviously dependent upon environmental conditions, is between the end of Jan. and Nov. of each year. 'Aires' is day neutral variety and the planting date generally extends to Oct. of the previous year. Maximum production tends to be in Apr. with a second peak in Oct.

*Planting date.*—Oct. 27, 1993.
10% *Flowering.*—Dec. 2, 1993.
*First mature fruits.*—Jan. 14, 1994.
*Maturity* (15–20 *gms/plant*).—Jan. 27, 1994.

Disease resistance: No special or particular sensitivity to disease or parasite has been noted for 'Aires'.

What is claimed is:

1. A new and distinct variety of strawberry plant, substantially as shown and described.

* * * * *

9079060

SELVA